United States Patent [19]

Jönsson et al.

[11] Patent Number: 5,160,625
[45] Date of Patent: Nov. 3, 1992

[54] METHOD FOR FLOW FIELD FLOW FRACTIONATION

[75] Inventors: Jan Å. Jönsson, Malmö; Alf Carlshaf, Lund, both of Sweden

[73] Assignee: Pharmacia LKB Biotechnology AB, Upsala, Sweden

[21] Appl. No.: 803,449

[22] Filed: Dec. 6, 1991

Related U.S. Application Data

[63] Continuation of Ser. No. 457,682, filed as PCT/SE89/00318, Jun. 5, 1989, abandoned.

[30] Foreign Application Priority Data

Jun. 8, 1988 [SE] Sweden ................ 8802126

[51] Int. Cl.$^5$ ............................................ B01D 15/08
[52] U.S. Cl. ...................... 210/635; 210/198.2; 210/321.89; 210/500.23; 210/637; 210/638; 210/656; 210/659
[58] Field of Search ............... 210/635, 656, 636, 637, 210/638, 659, 748, 96.2, 101, 321.69, 321.89, 406, 409, 416.1, 500.23; 427/245, 246; 73/61.1 C, 61.1 R, 865.5

[56] References Cited

U.S. PATENT DOCUMENTS

| | | | |
|---|---|---|---|
| 2,987,472 | 6/1961 | Kollsman | 210/652 |
| 4,147,621 | 4/1979 | Giddings | 210/143 |
| 4,214,981 | 7/1980 | Giddings | 210/748 |
| 4,285,810 | 8/1981 | Kirkland | 73/865.5 |
| 4,440,638 | 4/1984 | Judy | 210/748 |
| 4,481,808 | 11/1984 | Sakata et al. | 73/61.1 R |
| 4,623,470 | 11/1986 | Adler | 210/512.3 |
| 4,657,676 | 4/1987 | Keary | 210/198.2 |
| 4,657,742 | 4/1987 | Beaver | 210/198.2 |
| 4,737,268 | 4/1988 | Giddings | 210/748 |
| 4,748,205 | 10/1988 | Murakami | 210/500.23 |
| 4,787,974 | 11/1988 | Ambrus | 210/500.23 |
| 4,830,756 | 5/1989 | Giddings | 210/748 |
| 4,894,146 | 1/1990 | Giddings | 210/748 |
| 4,894,172 | 1/1990 | Williams | 210/748 |

FOREIGN PATENT DOCUMENTS

3043682 7/1981 Fed. Rep. of Germany ... 210/198.2

OTHER PUBLICATIONS

J. C. Giddings et al., "Fast Particle Separation by Flow/Steric Field-Flow Fractionation", Analytical Chemistry, 59, (1987), 15, pp. 1957–1962.
H.-L. Lee et al., "Single-Phase Chromatography: Solute Retardation by Ultrafiltration and Electrophoreses", AIChE Journal, 20, (1974); 4, pp. 776–784.
Chemical Abstracts, vol. 91, (1979), Abstract No. 195092r, Chem. Eng. Sci., 1979, 34(5), 725–31 (Eng).
Jonsson, J. A., Carlshaf, A., "Flor Field Fractionation in Hollow Cylindrical Fibers", Analytical Chemistry, 61, (1989):1, pp. 11–18.

*Primary Examiner*—Ernest G. Therkorn
*Attorney, Agent, or Firm*—Fred Philpitt

[57] ABSTRACT

An apparatus for flow field flow (FFF) fractionation comprises: a porous hollow fiber (1) which extends longitudinally between end-fittings (2, 3) of a tube (4), one end of said fiber (1) being connected to a first pump (5) for pumping a first carrier liquid into said fiber (1) via a valve (9) for introducing a liquid sample to be fractionated, the other end of said fiber (1) being connected to a container for a second carrier liquid via a flow-through detector (11), for detecting fractions of said sample; a second pump (12) which is connected to the interspace between the tube (4) and the fiber (1) to pump out carrier fluid through the porous fiber wall; and a control unit (6) which is adapted to control said first pump (5) to have a flower flow rate than said second pump (12) during injection and relaxation of the sample, and a higher flow rate than said second pump (12) to elute the sample; and a method for FFF fractionation in a hollow fiber utilizing the steps of sample application, relaxation, flow restoration, and elution whereby the radial flow out of the fiber is controlled by a separate pump.

8 Claims, 3 Drawing Sheets

METHOD FOR FLOW FIELD FLOW FRACTIONATION

This is a continuation of application Ser. No. 07/457,682, filed as PCT/SE89/00318, Jun. 5, 1989, now abandoned.

TECHNICAL FIELD

The invention relates to a method and an apparatus for flow field flow fractionation.

BACKGROUND OF THE INVENTION

Field flow fractionation (FFF), pioneered by Giddings (Sep. Sci. 1966, 1, 123) is a versatile family of separation methods related to liquid chromatography. Since none of the subtechniques are utilizing a stationary phase for separation and therefore do not depend on an equilibrium process like classical chromatography, FFF is not in a strict sense a member of the family of chromatographic techniques.

FFF involves the application of an external force field to a solution, causing a migration of its constituents towards the separation channel wall. Depending on the magnitude of the force field and on chemical/physical properties, a certain solute will eventually reach a certain concentration distribution resulting in a fixed distance from the separation channel wall, this process is called relaxation. If the solution in the channel is caused to move forward in a laminar way, a parabolic flow profile will develop and the constituents will move forward with velocities equal to that axial velocity vector where most of the solute is located.

The applied field may e.g. be thermal gradients (thermal FFF), centrifugal forces (sedimentation FFF), electrical forces (electrical FFF), transverse or lateral flow (flow FFF) and transverse pressure gradients (pressure FFF). The different field types in FFF have recently been described by Janca J. (Field Flow Fractionation, Marcel Dekker: New York, 1988; Chapter 3).

The most universal FFF technique is flow FFF, which has been explored for a wide range of characterisation problems, involving virus samples (Giddings, J. C.; Yang, F. J.; Myers, M. N., J. Virol. 1977, 21, 131), proteins (Giddings, J. C.; Yang, F. J.; Myers, M. N., Anal Biochem. 1977, 81, 395), and silica sols (Giddings, J. C.; Lin, G. C.; Myers, M. N., J. Coll. Interface Sci. 1978, 65, 67) as well as synthetic polymers of both lipophilic (Brimhall, S. L.; Myers, M. N.; Caldwell, K. D.; Giddings, J. C., J. Polym. Sci. Polym. Lett. Ed. 1984, 22, 339) and hydrophilic (Giddings, J. C.; Lin, G. C.; Myers, M. N., J. Liq. Chromatogr. 1978, 1, 1) nature.

Significant technical improvements in flow FFF have been made in recent years by Wahlund and Giddings with coworkers (Wahlund, K.-G.; Winegartner, H. S.; Caldwell, K. D.; Giddings, J. C., Anal. Chem. 1986, 58, 573; Wahlund, K.-G.; Giddings, J. C., Anal. Chem. 1987, 59, 1332; and Giddings, J. C.; Xiurong, C.; Wahlund, K.-G.; Myers, M. N., Anal. Chem. 1987, 59, 1957) who obtained shorter elution times and better resolution.

Pressure FFF is a subtechnique that is closely related to flow FFF. In both flow FFF and pressure FFF a cross-flow represents the lateral field and the separation channel is almost always of the parallel plane membrane type. The principal difference between flow FFF and pressure FFF is that in flow FFF, the flow field is applied externally across the channel by a separate pump, whereas in pressure FFF the lateral flow is created by a pressure drop over the semi-permeable membrane. In 1974, Lee et al (Lee, H.-L.; Reis, J. F. G.; Dohner, J.; Lightfoot, E. N., A. I. Ch. J. 1974, 20, 776) published a paper where the first experimental work with pressure FFF in a circular channel was presented.

Doshi et al (Doshi, M. R.; Gill, W. N., Chem. Engin. Sci. 1979, 34, 725) have shown that this method in theory is expected to give better resolution than both flow FFF and pressure FFF with parallel plane membranes.

BROAD DESCRIPTION OF THE INVENTION

One object of the invention is to bring about an apparatus for flow FFF in which the flow rates can be more precisely controlled, which, in addition to providing better accuracy, also permits the application of gradient elution techniques.

Another object of the invention is to bring about an apparatus which has better mechanical properties and is easier to connect to liquid chromatographic equipment than the apparatuses hitherto known.

Still another object of the invention is to provide an improved method for FFF utilizing said apparatus and which makes it possible to obtain considerably improved separation results.

This is attained in that the apparatus according to the invention is characterized in that a porous hollow fiber extends longitudinally between end-fittings of a tube, one end of said fiber being connected to a first pump for pumping a first carrier liquid into said fiber via a valve for introducing a liquid sample to be fractionated, the other end of said fiber being connected to a container for a second carrier liquid via a flow-through detector for detecting fractions of said sample, a second pump is connected to the interspace between the tube and the fiber to pump out carrier fluid through the porous fiber wall thereby permitting a direct control of the flow in radial direction in the fiber, and a control unit is adapted to control said first pump to have a lower flow rate than said second pump during injection and relaxation of the sample, and a higher flow rate than said second pump to elute the sample.

BRIEF DESCRIPTION OF DRAWING

The invention will be described more in detail below with reference to the accompanying drawings.

DETAILED DESCRIPTION OF THE INVENTION

Figure 1:
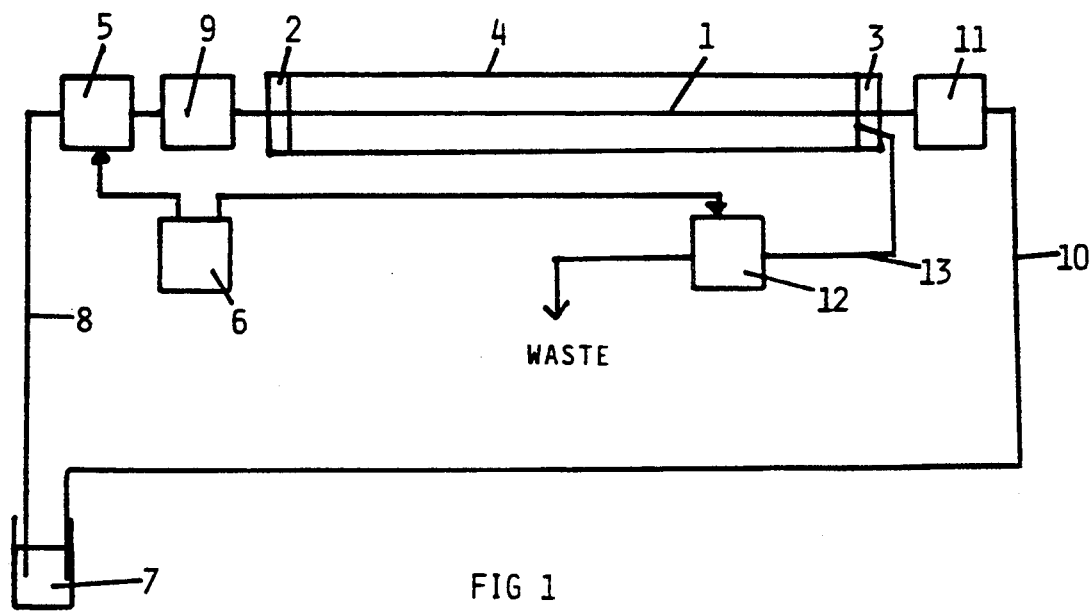
FIG. 1 schematically shows an embodiment of an apparatus according to the invention.

FIG. 1 shows one embodiment of an apparatus according to the invention.

A porous hollow fiber 1 extends longitudinally between the end-fittings 2 and 3, respectively, of a tube 4.

One end of the fiber 1 is connected to a pump 5 which is controlled by a control unit 6 to pump carrier liquid into the fiber 1 from a container 7 via a tubing 8 and a valve 9 through which a liquid sample to be fractionated can be introduced.

In the embodiment shown in FIG. 1 also the other end of the fiber 1 is connected to the container 7 via a tubing 10 and a flow-through detector 11 for detecting fractions of the sample introduced through the valve 9. It is to be understood that the tubing 10 equally well can be connected to a separate container (not shown) also containing a carrier liquid.

A pump 12 is via a tubing 13 connected to the interspace between the tube 4 and the fiber 1 through the end-fitting 3. The pump 12 is controlled by the control unit 6 and is adapted to pump out carrier fluid through the wall of the porous fiber 1 to waste.

The operation of the apparatus shown in FIG. 1 will be described with reference to FIG. 2 which shows the flow rates of the pumps 5 and 12, respectively, as a function of time as controlled by the control unit 6. The pump sequence is divided into four different phases where phase I is the sample introduction interval, phase II is the sample relaxation interval, phase III is the flow restoration interval and phase IV is the sample elution interval.

Figure 2:
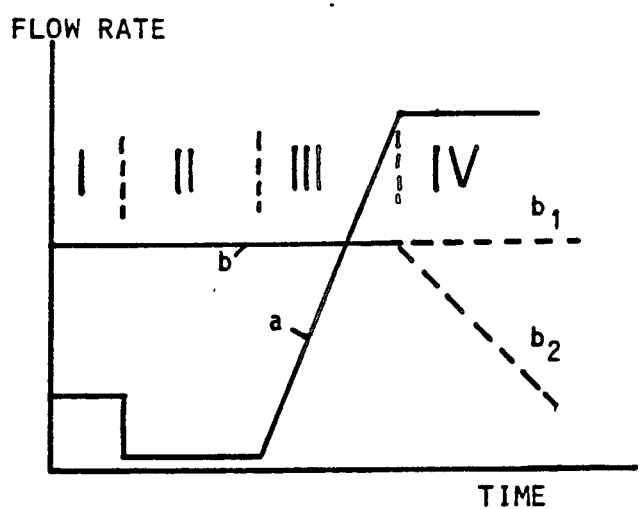
FIG. 2 is a flow rate versus time diagram for the pumps shown in FIG. 1.

In FIG. 2 the flow rate of the pump 5 is indicated by the curve a, while the flow rate of the pump 12 is indicated by the curve b.

As can be seen in FIG. 2 the flow rate b of the pump 12 is kept constant during the phases I, II and III. During the phase I, i.e. the sample injection interval, the flow rate a of the pump 5 is kept lower than the flow rate of the pump 12. During phase II, i.e. the sample relaxation interval, the flow rate a of the pump 5 may be reduced to be lower than during phase I. This means that during phases I and II the carrier liquid from the container 7 will flow backwards into the fiber 1 via the tubing 10 and the detector 11. At a certain point in the fiber 1, the axial flow will, thus, be zero. The position of this point, the relaxation point, will depend on the relation between the flow rates a and b. Molecules in the sample injected into the fiber 1 via the valve 9 will eventually concentrate and relax at this particular point.

The time needed for phase I (injection interval) is equal to the time needed to transport the sample from the injection valve to the relaxation point.

The time necessary for relaxation to be completed is equal to the time needed for the radial flow to transport a particle the maximum distance, i.e. from the centre of the fiber 1 to the fiber wall.

In phase III, i.e. the flow restoration interval, the flow rate a of the pump 5 is increased to the value which is used in elution of the sample. This value is higher than the still constant flow rate b of the pump 12.

In order not to contaminate the container 7 with the eluted sample, a three-way valve or two check valves (not shown) can easily be incorporated in the tubing 10 to supply the eluted sample to a further container (not shown).

In phase IV, i.e. the sample elution interval, the flow rate b of the pump 12 may still be kept constant as indicated by the dashed line $b_1$. In order to obtain a gradient elution of the sample the flow rate b of the pump 12 may be decreased during phase IV as indicated by the dashed line $b_2$. By this method the processing time in some cases can be considerably shortened.

The method according to the invention for separating sample constituents by FFF technique in a hollow fiber extending longitudinally between end-fittings of a tube, comprises the following phases, I-IV, which are characterized by the flow rate of a first pump 5, which is connected to one end of the fiber and which is controlled to pump liquid into the fiber, and the flow rate of a second pump 12, which is connected to the interspace between the fiber and the tube, and which is controlled to pump out fluid through the wall of the porous fiber to waste:

I (sample injection): the rate $b_I$ of the second pump 12 is kept at a value higher than the flow rate $a_I$ of the first pump 5. A sample is introduced via the longitudinal flow into the fiber. The sample accordingly enters the fiber but will not pass to the other end of it since $a_I < b_I$.

II (relaxation): the flow rate a of pump 5 is kept at a constant value $a_{II}$ well below the flow rate $b_{II}$ of pump 12, which is also kept constant so that the sample constituents concentrate and relax at the particular point in the fiber in which the longitudinal flow is zero. Optionally the flow $a_{II}$ is lower than $a_I$.

III (flow restoration): the flow rate $a_{III}$ of pump 5 is increased to a value higher than flow rate $b_{III}$ of pump 12, which means that the sample will start moving again against the end of the fiber.

IV (sample elution): the flow rate of pump 5 is kept at a value $a_{IV}$ which is higher than the flow rate $b_{IV}$ of pump 12. In order to obtain a gradient elution of the sample in the fiber the flow rate $b_{IV}$ could be decreased during this phase.

Optionally the flow rate of the second pump 12 is kept constant during the complete separation procedure.

EXAMPLE

A porous hollow fiber, either model H10-P100-20 with an inner diameter of 0.5 mm or model H5-P100-43 with a diameter of 1.1 mm (Amicon Inc., Danver, Mass., U.S.A.) was encapsulated in an empty, modified volume tube (model C16, Pharmacia AB, Uppsala, Sweden). A sample was injected with an internal volume (5 μl) injection valve (model 7410, Rheodyne Inc., Cotati, Calif., U.S.A.) equipped with a pneumatic control unit.

The detector was a fixed wavelength (254 nm) UV-detector (UV-1, Pharmacia AB, Uppsala, Sweden). The axial and the radial liquid flows were created by two syringe pumps (model P-500, Pharmacia AB, Uppsala, Sweden), connected to the fiber as shown in FIG. 1. The pumps were further connected to a computerized control unit (model LCC-500, Pharmacia AB, Uppsala, Sweden), which was programmed to control the pumps independently as well as the injection valve.

A buffer solution of 0,01M Tris HCl with 1 mM EDTA, 100 mM NaCl, 0,04% NaN$_3$ and 0,1% Triton X-100 at pH=7.0 served as carrier liquid in the separation of polystyrene latex beads. The same buffer, without Triton X-100, was used for the PUC-8.

A sample of two types of polystyrene latex beads with diameters 0.09 μm and 0.30 μm, respectively, (obtained from Sigma Chemical Company, St. Louis, Mo., U.S.A.) was introduced into the fiber with 0.5 mm inner diameter (phase I) with the axial flow at a constant rate of 30 μl/min. During the relaxation period (phase II), the axial flow was decreased to 6 μl/min. During 7 minutes, as calculated by theory, the sample molecules were allowed to migrate to their equilibrium distance from the fiber wall and the sample zone was axially compressed. In phase III, the axial flow was increased to 200 μl/min and kept at that value in phase IV. The radial flow was kept constant at 30 μl/min in all phases.

Figure 3:
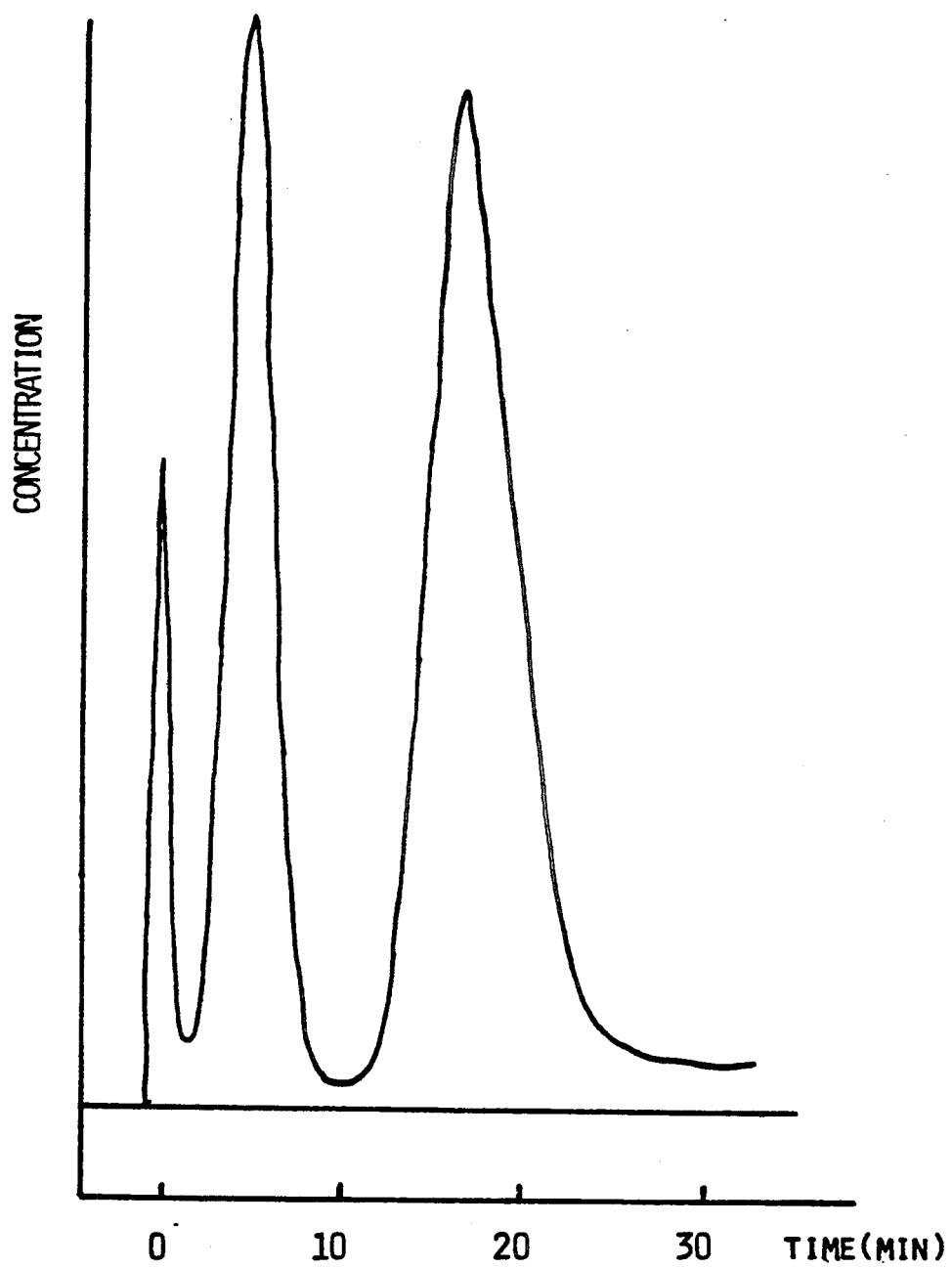
FIG. 3 shows a fractogram, i.e. a diagram of concentration versus time, illustrating the separation of two types of polystyrene latex beads.

The resulting separation is shown in FIG. 3. The two types of latex beads are completely separated, and emerge after retention times which are in good agreement with theoretically calculated values. The zone (peak) widths also agree with theoretical calculations.

In another experiment, a sample of the plasmid PUC-8 (obtained from the Molecular Biology Division, Pharmacia AB, Uppsala, Sweden) was introduced into the fiber with 1.1 mm inner diameter. During phase I, the axial flow was 80 $\mu$l/min. In phase II, lasting 12 min, the axial flow was decreased to 20 $\mu$l/min and the sample was allowed to equilibrate and concentrate as described above. In phase III, the axial flow was increased to 500 $\mu$l/min during 2 min and kept at that value in phase IV. The radial flow was kept constant at 100 $\mu$l/min in phases I–III and for 10 min from the start of phase IV, decreased in a linear way first to 80 $\mu$l/min after 15 min from the start of phase IV, and further to 20 $\mu$l/min after 60 min.

Figure 4:
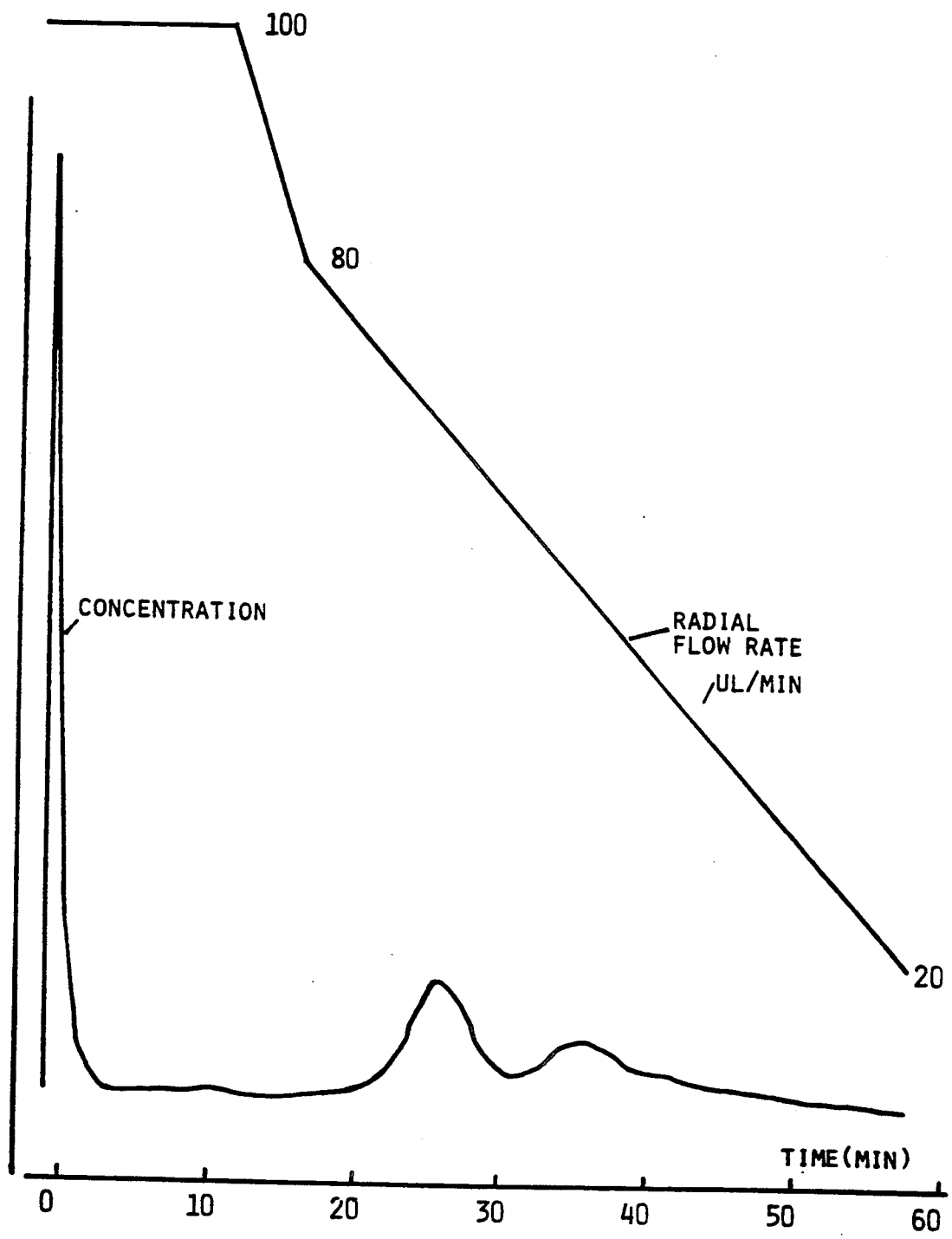
FIG. 4 shows a fractogram illustrating the separation of the plasmid PUC-8 from its dimer.

The resulting separation is shown in FIG. 4. Two peaks appear, which can be attributed to the plasmid PUC-8 (left peak) and to its dimer (right peak).

We claim:

1. A process for size separating sample constituents by the FFF technique in a porous hollow fiber extending longitudinally within and between the ends of a surrounding tube, the inlet end of said hollow fiber being connected to a first pump that pumps a liquid into the interior of the hollow fiber at a rate "a" that varies during the process, the outlet end of said hollow fiber being connected to a liquid reservoir, an interspace between said surrounding tube and said hollow fiber which is connected to a second pump having a suction flow rate "b" which is controlled to suck liquid radially outwardly through the wall of the porous hollow fiber to waste, comprising the sequential steps of
   I. introducing a sample to be size separated into the porous hollow fiber via the liquid pumped into the fiber by the first pump,
   II. maintaining the flow rate "a" of the liquid pumped into the inlet end of the fiber at a value less than the flow rate "b" of the liquid being sucked radially outwardly through the walls of the hollow fiber by the second pump which thereby causes liquid to flow from said reservoir back into the outlet end of the hollow fiber, thereby creating a flow rate gradient within the hollow fiber sufficient to permit concentration of the sample in the axial direction of the fiber for a period of time sufficient for equilibrating the constituents of the sample in a radial direction within the hollow fiber at different mean distances from the fiber wall according to particle size so that the larger sized constituents of the sample will concentrate near the fiber wall and the smaller sized constituents will concentrate toward the center of the hollow fiber,
   III. smoothly increasing the flow rate "a" to a flow rate higher than the flow rate "b" to thereby cause a net flow of liquid out of the outlet end of the hollow fiber, and
   IV. eluting the sample from the interior of the hollow fiber at a flow rate "a" that is maintained higher than flow rate "b", whereby the larger sized constituents of the sample that are concentrated near the wall of the hollow fiber, due to the lower axial flow near the fiber wall compared to the axial flow closer to the center of the hollow fiber, are retained in the hollow fiber for a longer period than the smaller sized particles of the sample that are not as close to the hollow fiber wall.

2. A method according to claim 1 wherein the flow rate of said second pump is kept constant during the entire separation procedure.

3. A method according to claim 1 wherein the flow rate of the second pump is decreased in step IV in order to obtain gradient elution of the sample.

4. A method according to claim 1 wherein the flow rate of the first pump during step II is less than the flow rate of the first pump in step I.

5. A process for size separating sample constituents by the FFF technique in a porous hollow fiber extending longitudinally within and between the ends of a surrounding tube, the inlet end of said hollow fiber being connected to a first pump that pumps a liquid into the interior of the hollow fiber at an interior flow rate that varies during the process, the outlet end of said hollow fiber being connected to a liquid reservoir, an interspace between said surrounding tube and said hollow fiber which is connected to a second pump having a suction flow rate which is controlled to suck liquid radially outwardly through the wall of the porous hollow fiber to waste, comprising the steps of
   I. in a first step introducing a sample to be size separated into the porous hollow fiber via the liquid pumped into the interior of the hollow fiber by the first pump,
   II. in a second step maintaining the interior flow rate of the liquid pumped into the inlet end of the fiber at a value less than the suction flow rate of liquid being sucked radially outwardly through the walls of the hollow fiber by the second pump to thereby cause liquid to flow from said reservoir back into the outlet end of the hollow fiber, thereby creating a flow rate gradient within the hollow fiber sufficient to position the sample in the axial direction of the fiber for a period of time sufficient for the constituents of the sample to distribute in a radial direction within the hollow fiber at different mean distances from the fiber wall according to particle size so that the larger sized constituents of the sample will concentrate toward the wall of the hollow fiber and the smaller sized constituents will concentrate toward the center of said hollow fiber,
   III. in a third step smoothly increasing the interior flow rate to a flow rate higher than said suction flow rate to thereby cause a net flow of liquid out of the outlet end of the hollow fiber, and
   IV. in a fourth step eluting the sample from the hollow fiber at an interior flow rate that is maintained higher than said suction flow rate, whereby due to the lower axial flow near the wall of the hollow fiber compared to the axial flow closer to the center of the hollow fiber the larger sized constituents of the sample that are concentrated near the fiber wall are retained in the hollow fiber for a longer period than the smaller sized constituents of the sample that are nearer the center of the hollow fiber.

6. A method according to claim 5 wherein the flow rate of said second pump is kept constant during the entire separation procedure.

7. A method according to claim 5 wherein the flow rate of the second pump is decreased in step IV in order to obtain gradient elution of the sample.

8. A method according to claim 5 wherein the flow rate of the first pump during step II is less than the flow rate of the first pump in step I.

* * * * *